US008884015B2

(12) United States Patent
Bou Chedid et al.

(10) Patent No.: US 8,884,015 B2
(45) Date of Patent: *Nov. 11, 2014

(54) PROCESS FOR THE PREPARATION OF A MONO-N-ALKYPIPERAZINE

(71) Applicant: BASF SE, Ludwigshafen (DE)

(72) Inventors: Roland Bou Chedid, Mannheim (DE); Johann-Peter Melder, Böhl-Iggelheim (DE); Ulrich Abel, Schifferstadt (DE); Roman Dostalek, Neuleiningen (DE); Bernd Stein, Alsbach-Hähnlein (DE)

(73) Assignee: BASF SE, Ludwigshafen (DE)

( * ) Notice: Subject to any disclaimer, the term of this patent is extended or adjusted under 35 U.S.C. 154(b) by 3 days.

This patent is subject to a terminal disclaimer.

(21) Appl. No.: 13/906,960

(22) Filed: May 31, 2013

(65) Prior Publication Data
US 2013/0324732 A1 Dec. 5, 2013

Related U.S. Application Data

(60) Provisional application No. 61/654,130, filed on Jun. 1, 2012.

(51) Int. Cl.
C07D 241/04 (2006.01)
C07D 295/00 (2006.01)
C07D 295/088 (2006.01)
C07D 295/03 (2006.01)
B01J 23/835 (2006.01)

(52) U.S. Cl.
CPC .......... C07D 295/088 (2013.01); C07D 295/03 (2013.01); B01J 23/835 (2013.01)
USPC .......................................... 544/404; 544/398

(58) Field of Classification Search
CPC .................................................. C07D 295/03
See application file for complete search history.

(56) References Cited

U.S. PATENT DOCUMENTS

| 3,166,558 | A | 1/1965 | Mascioli |
|---|---|---|---|
| 3,275,554 | A | 9/1966 | Wagenaark |
| 3,751,475 | A | 8/1973 | van der Voort et al. |
| 3,997,368 | A | 12/1976 | Petroff et al. |
| 4,014,933 | A | 3/1977 | Boettger et al. |
| 4,323,550 | A | 4/1982 | Goupil |
| 4,442,306 | A | 4/1984 | Mueller et al. |
| 4,739,051 | A | 4/1988 | Schroeder et al. |
| 4,832,702 | A | 5/1989 | Kummer et al. |
| 4,845,218 | A | 7/1989 | Schroeder |
| 4,851,578 | A | 7/1989 | Fischer et al. |
| 4,851,580 | A | 7/1989 | Mueller et al. |
| 4,910,304 | A | 3/1990 | Fischer et al. |
| 5,002,922 | A | 3/1991 | Irgang et al. |
| 5,110,928 | A | 5/1992 | Schroeder et al. |
| 5,463,130 | A | 10/1995 | Witzel et al. |
| 5,530,127 | A | 6/1996 | Reif et al. |
| 5,847,131 | A | 12/1998 | Simon et al. |
| 6,187,957 | B1 | 2/2001 | Meyer et al. |
| 6,448,457 | B1 | 9/2002 | Hesse et al. |
| 7,750,189 | B2 * | 7/2010 | Kubanek et al. ............... 564/480 |
| 8,436,169 | B2 | 5/2013 | Wigbers et al. |
| 8,450,530 | B2 | 5/2013 | Mueller et al. |
| 2003/0089591 | A1 | 5/2003 | Wolfert et al. |
| 2005/0000791 | A1 | 1/2005 | Wolfert et al. |
| 2007/0232833 | A1 | 10/2007 | Haese et al. |
| 2008/0064882 | A1 | 3/2008 | Huber-Dirr et al. |
| 2008/0255351 | A1 | 10/2008 | Hoffer et al. |
| 2008/0299390 | A1 | 12/2008 | Houssin et al. |
| 2009/0286977 | A1 | 11/2009 | Kubanek et al. |

(Continued)

FOREIGN PATENT DOCUMENTS

| CA | 1046166 A1 | 1/1979 |
|---|---|---|
| CA | 1055677 A1 | 6/1979 |

(Continued)

OTHER PUBLICATIONS

U.S. Appl. No. 13/906,931.

(Continued)

Primary Examiner — Andrew D Kosar
Assistant Examiner — John S Kenyon
(74) Attorney, Agent, or Firm — Drinker Biddle & Reath LLP

(57) ABSTRACT

Process for the preparation of a mono-N-alkylpiperazine of the formula I

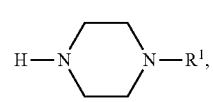

in which $R^1$ is $C_1$- to $C_5$-alkyl or 2-(2-hydroxyethoxy)ethyl, by reacting diethanolamine (DEOA) of the formula II

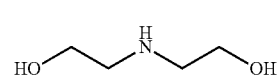

with a primary amine of the formula $H_2N-R^1$ (III) in the presence of hydrogen and a supported, metal-containing catalyst, where the catalytically active mass of the catalyst, prior to its reduction with hydrogen, comprises oxygen-containing compounds of aluminum, copper, nickel and cobalt and, in the range from 0.2 to 5.0% by weight, oxygen-containing compounds of tin, calculated as SnO, and the reaction is carried out in the liquid phase at an absolute pressure in the range from 95 to 145 bar.

32 Claims, No Drawings

(56) References Cited

U.S. PATENT DOCUMENTS

| | | |
|---|---|---|
| 2010/0274010 A1 | 10/2010 | Kubanek et al. |
| 2010/0274055 A1 | 10/2010 | Kubanek et al. |
| 2011/0054167 A1 | 3/2011 | Kubanek et al. |
| 2011/0137029 A1 | 6/2011 | Kubanek et al. |
| 2011/0137030 A1 | 6/2011 | Kubanek et al. |
| 2011/0172430 A1 | 7/2011 | Ernst et al. |
| 2011/0218270 A1 | 9/2011 | Suter et al. |
| 2011/0218323 A1 | 9/2011 | Dahmen et al. |
| 2011/0251433 A1 | 10/2011 | Wigbers et al. |
| 2011/0251434 A1 | 10/2011 | Muller et al. |
| 2011/0288337 A1 | 11/2011 | Chedid et al. |
| 2011/0288338 A1 | 11/2011 | Wigbers et al. |
| 2011/0294977 A1 | 12/2011 | Schaub et al. |
| 2012/0035049 A1 | 2/2012 | Kubanek et al. |
| 2012/0035399 A1 | 2/2012 | Abillard et al. |
| 2012/0095221 A1 | 4/2012 | Wigbers et al. |
| 2012/0157679 A1 | 6/2012 | Wigbers et al. |
| 2013/0331573 A1 * | 12/2013 | Bou Chedid et al. ......... 544/358 |

FOREIGN PATENT DOCUMENTS

| | | |
|---|---|---|
| CN | 102101847 A | 6/2011 |
| CN | 102304101 A | 1/2012 |
| DE | 917 784 C | 9/1954 |
| DE | 941 909 C | 4/1956 |
| DE | 1954546 A1 | 5/1971 |
| DE | 21 25039 A1 | 12/1971 |
| DE | 1953263 A1 | 2/1972 |
| DE | 2445303 A1 | 4/1976 |
| DE | 26 28 087 A1 | 1/1977 |
| DE | 2706826 A1 | 9/1977 |
| DE | 36 11 230 A1 | 10/1987 |
| DE | 4021230 | 1/1991 |
| DE | 4028295 A1 | 3/1992 |
| DE | 19809418 A1 | 9/1999 |
| DE | 19859776 A1 | 6/2000 |
| DE | 10218849 A1 | 11/2003 |
| EP | 70 512 A1 | 1/1983 |
| EP | 75940 A1 | 4/1983 |
| EP | 0137478 A2 | 4/1985 |
| EP | 0227904 A1 | 7/1987 |
| EP | 235651 A1 | 9/1987 |
| EP | 0257443 A1 | 3/1988 |
| EP | 382049 A1 | 8/1990 |
| EP | 0434062 A1 | 6/1991 |
| EP | 440829 A1 | 8/1991 |
| EP | 446783 A2 | 9/1991 |
| EP | 514 692 A2 | 11/1992 |
| EP | 552 463 A1 | 7/1993 |
| EP | 599 180 A1 | 6/1994 |
| EP | 673 918 A1 | 9/1995 |
| EP | 696572 A1 | 2/1996 |
| EP | 0816350 A1 | 1/1998 |
| EP | 1 312 599 A1 | 5/2003 |
| EP | 1 312 600 A1 | 5/2003 |
| GB | 1512797 A | 6/1978 |
| JP | 62145076 A | 6/1987 |
| WO | WO-92/04119 A1 | 3/1992 |
| WO | WO-03/051508 A1 | 6/2003 |
| WO | WO-2004/085356 A1 | 10/2004 |
| WO | WO-2005/110969 A1 | 11/2005 |
| WO | WO-2006/005505 A1 | 1/2006 |
| WO | WO-2006/114417 A2 | 11/2006 |
| WO | WO-2007/036496 A1 | 4/2007 |
| WO | WO-2008/006750 A1 | 1/2008 |
| WO | WO-2008/006754 A1 | 1/2008 |
| WO | WO-2009/027249 A2 | 3/2009 |
| WO | WO-2009080506 A1 | 7/2009 |
| WO | WO-2009080507 A1 | 7/2009 |
| WO | WO-2009080508 A1 | 7/2009 |
| WO | WO-2010/031719 A1 | 3/2010 |
| WO | WO-2010/052181 A2 | 5/2010 |
| WO | WO-2010/054988 A2 | 5/2010 |
| WO | WO-2010/069856 A1 | 6/2010 |
| WO | WO-2010/089265 A2 | 8/2010 |
| WO | WO-2010/089266 A2 | 8/2010 |
| WO | WO-2010/089346 A2 | 8/2010 |
| WO | WO-2010/103062 A1 | 9/2010 |
| WO | WO-2010/106133 A1 | 9/2010 |
| WO | WO-2010/115759 A2 | 10/2010 |
| WO | WO-2010/146009 A1 | 12/2010 |
| WO | WO-2011/067200 A1 | 6/2011 |
| WO | WO-2011067199 A1 | 6/2011 |
| WO | WO-2011/082967 A1 | 7/2011 |
| WO | WO-2011/082994 A1 | 7/2011 |
| WO | WO-2011/107512 A1 | 9/2011 |
| WO | WO-2011/115759 A1 | 9/2011 |
| WO | WO-2011157710 A1 | 12/2011 |
| WO | WO-2012049101 A1 | 4/2012 |
| WO | WO-2012055893 A1 | 5/2012 |

OTHER PUBLICATIONS

U.S. Appl. No. 13/910,602.
U.S. Appl. No. 13/910,554.
Database WPI, Week 198731, Thomson Scientific, London, GA; AN 1987-218358 (XP002664153), & JP 62 145076 A (KOA Corp) Jun. 29, 1987.
International Search Report for PCT/EP2011/059848—Jun. 14, 2011, dated Jul. 25, 2011.
International Search Report for PCT/EP2011/067612 dated Nov. 22, 2011.
International Search Report for PCT/EP2011/068700, mailed Feb. 17, 2012.
International Search Report for PCT/EP2013/060658, mailing date Jul. 15, 2013.

* cited by examiner

PROCESS FOR THE PREPARATION OF A MONO-N-ALKYPIPERAZINE

CROSS-REFERENCE TO RELATED APPLICATIONS

This application claims benefit (under 35 U.S.C. §119(e)) of U.S. Provisional Application 61/654,130, filed Jun. 1, 2012, which is incorporated herein by reference in its entirety.

BACKGROUND OF THE INVENTION

The present invention relates to a process for the preparation of a mono-N-alkylpiperazine of the formula I

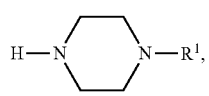

in which $R^1$ is $C_1$- to $C_5$-alkyl or 2-(2-hydroxyethoxy)ethyl, by reacting diethanolamine (DEOA) of the formula II

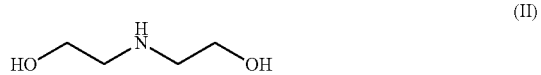

with a primary amine of the formula $H_2N-R^1$ (III) in the presence of hydrogen and a supported metal-containing catalyst.

The process products are used inter alia as intermediates in the production of fuel additives (U.S. Pat. No. 3,275,554 A; DE 21 25 039 A and DE 36 11 230 A), surfactants, drugs and crop protection agents, hardeners for epoxy resins, catalysts for polyurethanes, intermediates for producing quaternary ammonium compounds, plasticizers, corrosion inhibitors, synthetic resins, ion exchangers, textile auxiliaries, dyes, vulcanization accelerators and/or emulsifiers.

WO 03/051508 A1 (Huntsman Petrochemical Corp.) relates to processes for the amination of alcohols using specific Cu/Ni/Zr/Sn-containing catalysts which, in a further embodiment, comprise Cr instead of Zr (see page 4, lines 10-16). The catalysts described in this WO application comprise no aluminum oxide and no cobalt.

WO 2008/006750 A1 (BASF AG) relates to certain Pb, Bi, Sn, Sb and/or In-doped, zirconium dioxide-, copper-, nickel- and cobalt-containing catalysts and their use in processes for preparing an amine by reacting a primary or secondary alcohol, aldehyde and/or ketone with hydrogen and ammonia, a primary or secondary amine. Aluminum oxide supports are not taught.

WO 2009/080507 A1 (BASF SE) describes certain Sn and Co-doped, zirconium dioxide-, copper-, nickel- and cobalt-containing catalysts and their use in processes for preparing an amine by reacting a primary or secondary alcohol, aldehyde and/or ketone with hydrogen and ammonia, a primary or secondary amine. Aluminum oxide supports are not taught.

WO 2009/080506 A1 (BASF SE) describes certain Pb, Bi, Sn, Mo, Sb and/or P-doped, zirconium dioxide-, nickel- and iron-containing catalysts and their use in processes for preparing an amine by reacting a primary or secondary alcohol, aldehyde and/or ketone with hydrogen and ammonia, a primary or secondary amine. Aluminum oxide supports are not taught. Preferably, the catalysts comprise no Cu and no Co.

WO 2009/080508 A1 (BASF SE) teaches certain Pb, Bi, Sn and/or Sb-doped, zirconium dioxide-, copper-, nickel-, cobalt- and iron-containing catalysts and their use in processes for preparing an amine by reacting a primary or secondary alcohol, aldehyde and/or ketone with hydrogen and ammonia, a primary or secondary amine. Aluminum oxide supports are not taught.

WO 2011/067199 A1 (BASF SE) relates to certain aluminum oxide-, copper-, nickel-, cobalt- and tin-containing catalysts and their use in processes for the preparation of an amine from a primary or secondary alcohol, aldehyde and/or ketone. The preparation of N-methylpiperazine from DEOA and monomethylamine is mentioned in general terms on page 25, lines 20-21.

WO 2011/157710 A1 (BASF SE) describes the preparation of certain cyclic tertiary methylamines, where an amino alcohol from the group 1,4-aminobutanol, 1,5-aminopentanol, aminodiglycol (ADG) or aminoethylethanolamine is reacted with methanol at elevated temperature in the presence of a copper-containing heterogeneous catalyst in the liquid phase.

WO 2012/049101 A1 (BASF SE) relates to a process for the preparation of certain cyclic tertiary amines by reacting an amino alcohol from the group 1,4-aminobutanol, 1,5-aminopentanol, aminodiglycol (ADG) or aminoethylethanolamine with a certain primary or secondary alcohol at elevated temperature in the presence of a copper-containing heterogeneous catalyst in the liquid phase.

CN 102 101 847 A (Zhangjiagang Tianyou New Material Techn. Co., Ltd.) describes a two-stage synthesis for N-methyl-N-(2-chloroethyl)piperazine from aminodiglycol (ADG) via N-methylpiperazine as intermediate.

CN 102 304 101 A (Shaoxing Xingxin Chem. Co., Ltd.) relates to the simultaneous preparation of piperazine and N-alkylpiperazines by reacting N-hydroxyethyl-1,2-ethanediamine with primary $C_{1-7}$-alcohols in the presence of metallic catalysts.

EP 446 783 A2 (BASF AG) relates inter alia to the preparation of N-aryl-substituted piperazines by amination of corresponding N,N-di(2-hydroxyalkyl)-N-arylamines.

EP 235 651 A1 (BASF AG) teaches a process for the preparation of N-methylpiperazine from DEOA and methylamine in the presence of metal-containing supported catalysts, in particular Cu-containing catalysts.

BRIEF SUMMARY OF THE INVENTION

The object of the present invention was to improve the economic feasibility of processes to date for the preparation of mono-N-alkylpiperazines of the formula I and to overcome one or more disadvantages of the prior art. The aim was to find conditions which can be established in technical terms in a simple manner and which make it possible to carry out the process with high conversion, high yield, space-time yields (STY), selectivity coupled with simultaneously high mechanical stability of the catalyst molding and low "runaway risk".

[Space-time yields are given in "amount of product/
(catalyst volume·time)"(kg/($l_{cat.}$·h)) and/or
"amount of product/(reactor volume·time)"(kg/
($l_{reactor}$·h)].

A DETAILED DESCRIPTION OF THE INVENTION

Accordingly, a process for the preparation of a mono-N-alkylpiperazine of the formula I

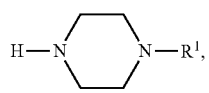

in which $R^1$ is to $C_1$- to $C_5$-alkyl or 2-(2-hydroxyethoxy)ethyl, by reacting diethanolamine (DEOA) of the formula II

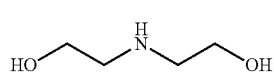

with a primary amine of the formula $H_2N-R^1$ (III) in the presence of hydrogen and a supported, metal-containing catalyst has been found, wherein the catalytically active mass of the catalyst, prior to its reduction with hydrogen, comprises oxygen-containing compounds of aluminum, copper, nickel and cobalt and, in the range from 0.2 to 5.0% by weight, oxygen-containing compounds of tin, calculated as SnO, and the reaction is carried out in the liquid phase at an absolute pressure in the range from 95 to 145 bar.

The radical $R^1$ is 2-(2-hydroxyethoxy)ethyl or $C_{1-5}$-alkyl, preferably $C_{1-3}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, particularly preferably methyl, ethyl and 2-(2-hydroxyethoxy)ethyl. The primary amine III is correspondingly particularly preferably monomethylamine, monoethylamine or 1-amino-2-(2-hydroxyethoxy)ethane (aminodiglycol, ADG).

Preferably preparable with the process according to the invention are amines of the formula I

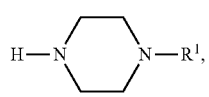

in which $R^1$=methyl, ethyl or 2-(2-hydroxyethoxy)ethyl.

In particular, catalysts whose catalytically active mass, prior to its reduction with hydrogen, comprises in the range from
15 to 80% by weight of oxygen-containing compounds of aluminum, calculated as $Al_2O_3$,
1 to 20% by weight of oxygen-containing compounds of copper, calculated as CuO,
5 to 35% by weight of oxygen-containing compounds of nickel, calculated as NiO,
5 to 35% by weight of oxygen-containing compounds of cobalt, calculated as CoO, and
0.2 to 5.0% by weight of oxygen-containing compounds of tin, calculated as SnO, are used in the abovementioned amination process.

The process can be carried out continuously or discontinuously. Preference is given to a continuous procedure.

In the circulating-gas procedure, the starting materials (DEOA, the primary amine III) are evaporated in a circulating-gas stream and passed to the reactor in gaseous form. The starting materials (DEOA, the primary amine III) can also be evaporated as aqueous solutions and be passed with the circulating-gas stream to the catalyst bed.

Preferred reactors are tubular reactors. Examples of suitable reactors with circulating-gas stream can be found in Ullmann's Encyclopedia of Industrial Chemistry, 5th ed., vol. B 4, pages 199-238, "Fixed-Bed Reactors".

Alternatively, the reaction takes place advantageously in a tube-bundle reactor or in a mono-stream plant.

In a mono-stream plant, the tubular reactor in which the reaction takes place can consist of a serial connection of a plurality (e.g. two or three) of individual tubular reactors. Optionally, an intermediate introduction of feed (comprising the DEOA and/or primary amine III and/or $H_2$) and/or circulating gas and/or reactor discharge from a downstream reactor is advantageously possible here.

The circulating-gas amount is preferably in the range from 40 to 1500 $m^3$ (at atmospheric pressure)/[$m^3$ of catalyst (bed volume)·h], in particular in the range from 100 to 1000 $m^3$ (at atmospheric pressure)/[$m^3$ of catalyst (bed volume)·h]. (Atmospheric pressure=1 bar abs.).

The circulating gas comprises preferably at least 10, particularly 50 to 100, very particularly 80 to 100, % by volume of hydrogen ($H_2$).

In the process according to the invention, the catalysts are used preferably in the form of catalysts which consist only of catalytically active mass and optionally a shaping auxiliary (such as e.g. graphite or stearic acid), if the catalyst is used as moldings, i.e. comprise no further catalytically active accompanying substances.

In this connection, the oxidic support material aluminum oxide ($Al_2O_3$) is deemed as belonging to the catalytically active mass.

The catalysts are used by introducing the catalytically active mass, ground to powder, into the reaction vessel, or by arranging the catalytically active mass, after grinding, mixing with shaping auxiliaries, shaping and heat-treating, in the reactor, in the form of catalyst moldings—for example as tablets, beads, rings, extrudates (e.g. strands).

The concentration data (in % by weight) of the components of the catalyst refer in each case—unless stated otherwise—to the catalytically active mass of the completed catalyst after its last heat treatment and before its reduction with hydrogen.

The catalytically active mass of the catalyst, after its last heat treatment and before its reduction with hydrogen, is defined as the sum of the masses of the catalytically active constituents and of the aforementioned catalyst support materials and comprises essentially the following constituents: aluminum oxide ($Al_2O_3$), oxygen-containing compounds of copper, nickel and cobalt, and oxygen-containing compounds of tin.

The sum of the aforementioned constituents of the catalytically active mass is usually 70 to 100% by weight, preferably 80 to 100% by weight, particularly preferably 90 to 100% by weight, particularly >95% by weight, very particularly preferably >98% by weight, in particular >99% by weight, e.g. particularly preferably 100% by weight.

The catalytically active mass of the catalysts according to the invention and used in the process according to the invention may further comprise one or more elements (oxidation state 0) or inorganic or organic compounds thereof, selected from groups I A to VI A and I B to VII B and VIII of the Periodic Table of the Elements.

Examples of such elements and their compounds are: transition metals, such as Mn and $MnO_2$, W and tungsten oxides, Ta and tantalum oxides, Nb and niobium oxides or niobium oxalate, V and vanadium oxides and vanadyl pyrophosphate; lanthanides, such as Ce and $CeO_2$ or Pr and $Pr_2O_3$; alkaline earth metal oxides, such as SrO; alkaline earth metal carbonates, such as $MgCO_3$, $CaCO_3$ and $BaCO_3$; boron oxide ($B_2O_3$).

Preferably, the catalytically active mass of the catalysts according to the invention and used in the process according to the invention comprises no rhenium, no ruthenium, no iron and/or no zinc, in each case neither in metallic (oxidation state=0) nor in an ionic (oxidation state≠0), in particular oxidized, form.

Preferably, the catalytically active mass of the catalysts according to the invention and used in the process according to the invention comprises no silver and/or molybdenum, in each case neither in metallic (oxidation state=0) nor in an ionic (oxidation state≠0), in particular oxidized, form.

In a particularly preferred embodiment, the catalytically active mass of the catalysts according to the invention and used in the process according to the invention comprises no further catalytically active component, neither in elemental (oxidation state=0) nor in ionic (oxidation state≠0) form. In the particularly preferred embodiment, the catalytically active mass is not doped with further metals or metal compounds.

However, customary accompanying trace elements originating from the metal extraction of Cu, Co, Ni and Sn are preferably excluded from this.

The catalytically active mass of the catalyst preferably does not comprise any oxygen-containing compounds of silicon, zirconium, titanium and/or chromium.

Prior to its reduction with hydrogen, the catalytically active mass of the catalyst comprises in the range from 0.2 to 5.0% by weight, particularly in the range from 0.4 to 4.0% by weight, more particularly in the range from 0.6 to 3.0% by weight, more particularly preferably in the range from 0.7 to 2.5% by weight, of oxygen-containing compounds of tin, calculated as SnO.

Prior to its reduction with hydrogen, the catalytically active mass of the catalyst comprises preferably in the range from 5.0 to 35% by weight, particularly in the range from 10 to 30% by weight, more particularly in the range from 12 to 28% by weight, very particularly 15 to 25% by weight, of oxygen-containing compounds of cobalt, calculated as CoO.

Prior to its reduction with hydrogen, the catalytically active mass of the catalyst further preferably comprises in the range from
15 to 80% by weight, particularly 30 to 70% by weight, more particularly 35 to 65% by weight, of oxygen-containing compounds of aluminum, calculated as $Al_2O_3$,
1 to 20% by weight, particularly 2 to 18% by weight, more particularly 5 to 15% by weight, of oxygen-containing compounds of copper, calculated as CuO, and
5 to 35% by weight, particularly 10 to 30% by weight, more particularly 12 to 28% by weight, very particularly 15 to 25% by weight, of oxygen-containing compounds of nickel, calculated as NiO.

The molar ratio of nickel to copper is preferably greater than 1, more preferably greater than 1.2, more particularly in the range from 1.8 to 8.5.

The BET surface area (ISO 9277:1995) of the catalysts according to the invention and used in the process according to the invention is preferably in the range from 30 to 250 $m^2/g$, particularly in the range from 90 to 200 $m^2/g$, more particularly in the range from 130 to 190 $m^2/g$, (in each case prior to the reduction with hydrogen). These ranges are achieved in particular by calcining temperatures during catalyst production in the range from 400 to 600° C., particularly 420 to 550° C. (cf. below).

Various processes are possible for producing the catalysts used in the process according to the invention. The catalysts are obtainable, for example, by peptizing pulverulent mixtures of the hydroxides, carbonates, oxides and/or other salts of the components with water and subsequently extruding and heat-treating the composition obtained in this way.

For the production of the catalysts according to the invention it is preferred to employ precipitation methods. Thus, for example, the catalysts can be obtained by coprecipitation of the nickel, cobalt, copper and Sn components from an aqueous salt solution comprising these elements, by means of bases, in the presence of a slurry of a sparingly soluble, oxygen-containing aluminum compound, and subsequent washing, drying and calcining of the resultant precipitate. As sparingly soluble, oxygen-containing aluminum compounds it is possible to use, for example, aluminum oxide, aluminum oxide hydrate, aluminum phosphates, aluminum borates and aluminum silicates. The slurries of the sparingly soluble aluminum compounds can be prepared by suspending finely particulate powders of these compounds in water with vigorous stirring. These slurries are advantageously obtained by precipitation of the sparingly soluble aluminum compounds from aqueous aluminum salt solutions by means of bases.

The catalysts according to the invention are preferably produced via a coprecipitation (mixed precipitation) of all of their components. For this purpose, an aqueous salt solution comprising the catalyst components is advantageously admixed, hot and with stirring, with an aqueous base—for example, sodium carbonate, sodium hydroxide, potassium carbonate or potassium hydroxide—until precipitation is complete. It is also possible to work with alkali metal-free bases such as ammonia, ammonium carbonate, ammonium hydrogencarbonate, ammonium carbamate, ammonium oxalate, ammonium malonate, urotropine, urea, etc. The nature of the salts used is generally not critical: since with this procedure it is the water-solubility of the salts that is of principal importance, one criterion is for the salts to have the good water-solubility required for preparing these relatively highly concentrated salt solutions. It is considered to be self-evident that when selecting the salts of the individual components, the salts selected will naturally only be salts with anions that do not lead to interference, whether by causing unwanted precipitations or by forming complexes and so preventing or hindering precipitation.

The precipitates obtained in these precipitation reactions are generally chemically nonuniform and consist, among other components, of mixtures of the oxides, oxide hydrates, hydroxides, carbonates and insoluble and basic salts of the metals used. In terms of the filterability of the precipitates, it may be advantageous for them to be aged, i.e. for them to be left to stand for some time after the precipitation, optionally in hot conditions or with air being passed through.

The precipitates obtained by these precipitation processes are processed further in a conventional way to form the catalysts according to the invention. First of all, the precipitates are washed. Via the duration of the washing procedure and via the temperature and amount of the wash water it is possible to influence the amount of alkali metal supplied by the (mineral) base possibly used as precipitant. Generally speaking, prolonging the washing time or increasing the temperature of the wash water will reduce the amount of alkali metal. After it has been washed, the precipitated material is generally dried at 80 to 200° C., preferably at 100 to 150° C., and subsequently calcined. The calcining is performed in general at temperatures between 300 and 800° C., preferably at 400 to 600° C., more particularly at 420 to 550° C.

The catalysts according to the invention can also be produced by impregnating aluminum oxide ($Al_2O_3$), which is present, for example, in the form of powder or moldings, such as extrudates/strands, tablets, beads or rings.

The aluminum oxide is used in the amorphous, gamma, theta and/or delta form, in the form of aluminum oxohydroxide (boehmite), preferably in the amorphous form.

Shaped bodies can be produced in accordance with the customary methods.

Impregnation takes place likewise in accordance with the customary methods, as described, for example, in A. B. Stiles, Catalyst Manufacture—Laboratory and Commercial Preparations, Marcel Dekker, New York (1983), by application of an appropriate metal salt solution in one or more impregnation stages, using as metal salts, for example, corresponding nitrates, acetates or chlorides. The composition is dried after the impregnation, and optionally calcined.

Impregnation may be carried out in accordance with the "incipient wetness" method, in which the aluminum oxide, in accordance with its water absorption capacity, is moistened at most to saturation point with the impregnation solution. However, impregnation may also take place in a supernatant solution.

In the case of multistage impregnating processes, it is advantageous to carry out drying and optionally calcining between individual impregnation steps. Multistage impregnation is particularly advantageous when a relatively large amount of metal is to be applied to the aluminum oxide.

To apply the metal components to the aluminum oxide, the impregnation can be carried out with all metal salts simultaneously or with the individual metal salts in succession in any order.

Subsequently, the catalysts produced by impregnation are dried and preferably also calcined, e.g. at the calcining temperature ranges already indicated above.

After calcining has taken place, the catalyst is usefully conditioned, whether by bringing it to a defined particle size by grinding or else mixing it, after grinding, with shaping auxiliaries such as graphite or stearic acid, compressing it into shapes—e.g. tablets—by means of a press, and carrying out heat treatment. The heat treatment temperatures in this case correspond preferably to the temperatures for calcining.

The catalysts produced in this way comprise the catalytically active metals in the form of a mixture of their oxygen-containing compounds, i.e. in particular as oxides and mixed oxides.

The catalysts produced for example as described above are stored and optionally traded as such. Before being used as catalysts, they are usually subjected to preliminary reduction. However, they can also be used without preliminary reduction, in which case they are then reduced by the oxygen present in the reactor under the conditions of the hydrogenative amination.

For the preliminary reduction, the catalysts are initially exposed to a nitrogen-hydrogen atmosphere at preferably 150 to 200° C. over a time of, for example, 12 to 20 hours, and are subsequently treated for up to a further 24 hours approximately at preferably 200 to 400° C. in a hydrogen atmosphere. In the course of this preliminary reduction, a part of the oxygen-containing metal compounds present in the catalysts is reduced to the corresponding metals, and so these metals are present together with the various oxygen compounds in the active form of the catalyst.

The process according to the invention is preferably carried out continuously, the catalyst preferably being arranged as a fixed bed in the reactor. In this connection, flow through the fixed catalyst bed from above and also from below is possible.

The primary amine III is used preferably in a 0.5- to 20-fold molar amount, particularly in a 5- to 15-fold molar amount, further particularly in a 6- to 13-fold molar amount, in particular in a 7- to 10-fold molar amount, e.g. an 8- to 10-fold molar amount, in each case based on the DEOA used. Particularly preferably, in the case of aminodiglycol (ADG) as primary amine III, the primary amine is used in a 0.5- to 2-fold, in particular in a 0.6- to 1.2-fold, molar amount, in each case based on the DEOA used.

The primary amine III can be used as aqueous solution, particularly as 30 to 95% strength by weight aqueous solution, e.g. also 65 to 90% strength by weight aqueous solution. Monomethylamine and monoethylamine are preferably also used without further solvent (compressed gas, purity particularly 95 to 100% strength by weight).

The starting material DEOA is preferably used as aqueous solution, particularly as 75 to 95% strength by weight aqueous solution, e.g. as 80 to 85% strength by weight aqueous solution.

Preferably, an offgas amount of from 5 to 800 cubic meters (stp)/(cubic meters of catalyst·h), in particular 20 to 300 cubic meters (stp)/($m^3$ of catalyst·h) is processed.

[Cubic meters (stp)=volume converted to standard temperature and pressure conditions(20° C.,1 bar abs.)].

Catalyst volume data always refers to the bulk volume.

The amination of the primary alcohol groups of the starting material DEOA is carried out in the liquid phase. Preferably, the fixed bed process is in the liquid phase.

In the case of the continuous fixed bed process in the liquid phase, the following process configuration, which has inter alia a particularly advantageous effect on the catalyst performance, is particularly preferred. The starting materials (DEOA, primary amine III) including hydrogen are passed over the catalyst firstly at a temperature in the range from 80 to 160° C., preferably 100 to 140° C., particularly preferably 110 to 130° C., and then, e.g. after 1 to 240 min, preferably 5 to 120 min, particularly preferably 10 to 90 min, further particularly preferably 20 to 60 min, the temperature is increased to 180 to 220° C., particularly 180 to 215° C., preferably 185 to 210° C., in particular 190 to 200° C. Accordingly, a start-up procedure at lower temperatures is connected upstream. The reaction product resulting from the start-up procedure can be discarded or returned to the reaction.

When working in the liquid phase, the starting materials (DEOA, primary amine III) are passed, preferably simultaneously, in liquid phase at pressures of from 9.5 to 14.5 MPa (95 to 145 bar), preferably 10.0 to 14.0 MPa, further preferably 10.5 to 13.5 MPa, further preferably 11.0 to 13.0 MPa, particularly preferably 11.5 to 12.5 MPa, and at temperatures of in general 180 to 220° C., particularly 180 to 215° C., preferably 185 to 210° C., in particular 190 to 200° C., including hydrogen over the catalyst, which is usually located in a fixed-bed reaction heated preferably from the outside. Here, both a trickle mode and also a liquid-phase mode is possible. The catalyst hourly space velocity is generally in the range from 0.2 to 0.8, preferably 0.3 to 0.7, particularly preferably 0.4 to 0.6, further preferably 0.4 to 0.5 kg of DEOA per liter of catalyst (bed volume) and per hour (DEOA calculated as 100% strength). Optionally, the starting materials can be diluted with a suitable solvent, such as water, tetrahydrofuran, dioxane, N-methylpyrrolidone or ethylene glycol dimethyl ether. It is expedient to heat the reactants even before they are introduced into the reaction vessel, preferably to the reaction temperature.

The reaction is preferably carried out at a catalyst hourly space velocity in the range from 40 to 1500 liters (stp) of hydrogen/($l_{cat.}$·h), particularly a catalyst hourly space velocity in the range from 100 to 1000 liters of hydrogen (stp)/($l_{cat.}$·h).

[Liters (stp)=l (stp)volume converted to standard temperature and pressure conditions(20° C.,1 bar abs.)]

The pressure in the reaction vessel which arises from the sum of the partial pressures of the primary amine III, of the DEOA and of the reaction products formed, and also optionally of the co-used solvent at the stated temperatures, is expediently increased to the desired reaction pressure by injecting hydrogen.

In the case of continuous operation in the liquid phase, the excess primary amine III can be circulated together with the hydrogen.

If the catalyst is arranged as a fixed bed, it can be advantageous for the selectivity of the reaction to mix the catalyst moldings in the reactor with inert packings, to "dilute" them so to speak. The fraction of packings in such catalyst preparations can be 20 to 80, particularly 30 to 60 and in particular 40 to 50, parts by volume.

The water of reaction formed in the course of the reaction (in each case one mole per mole of reacted alcohol group) generally does not have a disruptive effect on the degree of conversion, the rate of reaction, the selectivity and the service life of the catalyst and is therefore expediently only removed upon working-up the reaction product, e.g. by distillation.

After the reaction discharge has expediently been decompressed, the excess hydrogen and the optionally present excess aminating agents are removed therefrom and the crude reaction product obtained is purified, e.g. by means of fractional rectification. Suitable work-up methods are described e.g. in EP 1 312 600 A and EP 1 312 599 A (both BASF AG). The excess primary amine and the hydrogen are advantageously returned again to the reaction zone. The same applies for any incompletely reacted DEOA.

A work-up of the product of the reaction is preferably as follows:

From the reaction product of the reaction, by means of distillation, (i) firstly optionally unreacted primary amine III, $R^1$ preferably=$C_1$- to $C_5$-alkyl, is separated off overhead, (ii) water is separated off overhead, (iii) optionally present by-products with a lower boiling point than that of the process product I (low boilers) are separated off overhead, (iv) the process product mono-N-alkylpiperazine I is separated off overhead, with optionally present by-products with a higher boiling point than that of the process product I (high boilers) and optionally present unreacted DEOA (II) remaining in the bottom.

During the reaction of the process according to the invention, the alkylaminoethylethanolamine of the formula IV

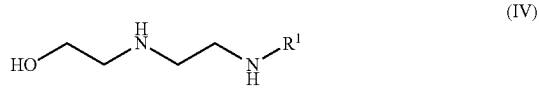

(IV)

can be formed as by-product:

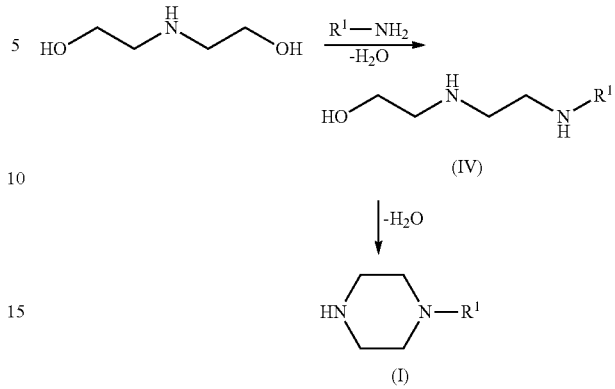

Therefore, in particular by means of distillation,
(v) from the bottom of step iv, optionally present unreacted DEOA (II) and/or optionally present alkylaminoethylethanolamine as by-product with the formula IV are separated off overhead and returned to the reaction.

Primary amine III separated off in step i and having a purity of from 90 to 99.9% by weight, particularly 95 to 99.9% by weight, is preferably returned to the reaction where further preferably some of the separated-off amine III, particularly 1 to 30% by weight of the separated-off amine III, further particularly 5 to 25% by weight of the separated-off amine III, is removed.

A work-up of the product of the reaction of aminodiglycol (ADG), i.e. $R^1$=2-(2-hydroxyethoxy)ethyl, with DEOA is preferably as follows:

From the reaction product of the reaction, by means of distillation
(i) firstly water is separated off overhead,
(ii) optionally unreacted ADG is separated off overhead,
(iii) optionally present by-products with a lower boiling point than that of the process product I (low boilers) are separated off overhead,
(iv) the process product mono-N-alkylpiperazine I is separated off overhead, with optionally present by-products with a higher boiling point than that of the process product I (high boilers) and optionally present unreacted DEOA (II) remaining in the bottom.

In particular, by means of distillation,
(v) from the bottom of step iv, optionally present unreacted DEOA (II) and/or optionally present alkylaminoethylethanolamine as by-product with the formula IV are separated off overhead and returned to the reaction.

ADG separated off in step ii and having a purity of from 90 to 99.9% by weight, particularly 95 to 99.9% by weight, is preferably returned to the reaction, where further preferably some of the separated-off ADG, particularly 1 to 30% by weight of the separated-off ADG, further particularly 5 to 25% by weight of the separated-off ADG, is removed.

All pressure data refer to the absolute pressure.
All ppm data refer to the mass.

EXAMPLES

1. Preparation of Catalyst A [=Example 4 in WO 2011/067199 A (BASF SE)]

An aqueous solution of nickel nitrate, cobalt nitrate, copper nitrate, aluminum nitrate and tin(II) chloride, containing 3.9% by weight Ni, 3.9% by weight Co, 1.9% by weight Cu, 5.5% by weight $Al_2O_3$ and 0.5% by weight Sn, was precipitated simultaneously in a stirred vessel in a constant stream with a 20% strength by weight aqueous sodium carbonate solution at a temperature of 65-70° C. in such a way that the pH, measured with a glass electrode, was maintained at 5.7. Following the precipitation, air was blown in for 1 hour, after which the pH of the solution was adjusted to a level of 7.4 using sodium carbonate solution. The resulting suspension was filtered and the filter cake was washed with fully demineralized water until the electrical conductivity of the filtrate was about 20 mS. Thereafter the filter cake was dried in a drying cabinet at a temperature of 150° C. The hydroxide/carbonate mixture obtained in this way was then calcined at a temperature of 500° C. for 4 hours. The catalyst material was subsequently mixed with 3% by weight of graphite and shaped to form tablets measuring 3×3 mm. The tablets obtained in this way are reduced in hydrogen at a temperature of 280-300° C. for at least 12 hours. The passivation of the reduced catalyst was carried out at room temperature in diluted air (air in $N_2$ with an $O_2$ content of not more than 5% by volume). The composition of the resulting catalyst was as shown in table I below.

TABLE I

| Catalyst *) | Ni % | Co % | Cu % | Sn % | BET **) $m^2/g$ | Support |
|---|---|---|---|---|---|---|
| Catalyst A | 18.6 | 17.3 | 10.6 | 1.1 | 187 | $Al_2O_3$ |

*) Catalyst composition in % by weight; remainder to 100% by weight is the support
**) ISO 9277: 1995

2. Reaction of DEOA with Monomethylamine (MMA) in a Continuously Operated Tubular Reactor A heated tubular reactor with an internal diameter of 14 mm, a centrally installed thermocouple and a total volume of 1000 ml was filled in the lower section with a bed of glass beads (250 ml), on top of this 500 ml of catalyst A and finally the remainder was filled again with glass beads. Prior to the reaction, the catalyst was activated under atmospheric pressure for 24 hours at max. 280° C. under hydrogen (25 l (stp)/h) (l (stp)=liters at standard temperature and pressure=volume converted to standard temperature and pressure conditions (20° C., 1 bar abs.)). 300 g/h of DEOA (85% strength aqueous), 600 g/h of the primary amine and 200 l (stp)/h of hydrogen were metered through the reactor from bottom to top. The reactor was held at a temperature of approx. 185 to 200° C. and a total pressure of 80-200 bar. The reaction temperature was selected such that a DEOA conversion of >90% was reached. The mixture leaving the reactor was cooled and decompressed to atmospheric pressure. At various times, samples were taken from the reaction mixture and analyzed by means of gas chromatography. For this, an "RTX-5 Amine" GC column 30 m in length was used, with a temperature program: 70° C./5 min, heat to 280° C. at a rate of 5° C./min, at 280° C./10 minutes.

At 200 bar, with 400 l (stp)/(l·h) of hydrogen, a molar ratio (MR) of MMA:DEOA of 10 and a DEOA space velocity of 0.5 kg/(l·h) (calculated on a 100% basis, as an 85% strength solution), after attainment of a temperature of 195° C., in 25 minutes, a runaway reaction was observed: the temperature climbed spontaneously to 253° C. and the pressure to 268 bar. Under these conditions, decomposition takes place and gases (such as methane) are formed which lead to the increase in pressure. From the safety standpoint, these conditions cannot be sustainably implemented. In other experiments under a reduced pressure of, for example, about 120 bar, runaway reactions of this kind were not observed.

At 80 bar, with 400 l (stp)/(l·h) of hydrogen, a molar ratio (MV) of MMA:DEOA of 10 and a DEOA space velocity of 0.5 kg/(l·h) (calculated on a 100% basis, as an 85% strength solution), at a temperature of 195° C. and a pressure of only 80 bar, a drop in selectivity (with respect to N-methyl-PIP) was observed.

The results of the experiments at 80-120 bar can be found in table II below. The bottom part of the table shows the compositions of the reaction discharges as per GC analysis.

TABLE II

| | Cat. | Pressure bar | $H_2$ l (stp)/ (l·h) | MR MMA:DEOA mol/mol | Temp. ° C. | DEOA feed*) | Hourly space velocity calc. 100% strength DEOA kg/(l·h) | Conversion of DEOA mol % | Sel. NMePIP based on DEOA mol % |
|---|---|---|---|---|---|---|---|---|---|
| Ex 1 | A | 120 | 150 | 10 | 195 | 85% strength | 0.5 | 88 | 72 |
| Ex 2 | A | 120 | 400 | 10 | 195 | 85% strength | 0.5 | 97 | 73 |
| Ex 3 | A | 120 | 400 | 12 | 195 | 85% strength | 0.5 | 90 | 71 |
| Ex 4 | A | 80 | 400 | 10 | 195 | 85% strength | 0.5 | 91 | 62 |

| | Low boilers | Piperazine | NMePIP | Dimethyl-piperazine | DEOA | Compound IV | High boilers |
|---|---|---|---|---|---|---|---|
| Ex 1 | 6.9% | 1.6% | 63.4% | 0.8% | 12.4% | 9.5% | 5.5% |
| Ex 2 | 7.5% | 1.6% | 70.8% | 0.9% | 2.5% | 6.6% | 10.1% |
| Ex 3 | 8% | 1.3% | 63.9% | 0.7% | 10.6% | 8.0% | 7.5% |
| Ex 4 | 9.3% | 1.7% | 56.4% | 1.6% | 9.2% | 12.6% | 9.2% |

Cat.: Catalyst
Temp.: Temperature in the reactor
Hourly space velocity: Catalyst hourly space velocity [kg of DEOA/(liter$_{cat.}$ · h)]
MR: Molar ratio in the feed
Sel.: Selectivity
NMePIP: Monomethylpiperazine (N-methyl-PIP)
*) Aqueous solution, in % by weight 3. Reaction of DEOA with Aminodiglycol (ADG, 1-Amino-2-(2-Hydroxyethoxy)Ethane) in a Batch Reactor A batch reactor with stirrer, a thermocouple and a total volume of 300 ml was filled with 7.5 g of activated catalyst.

For this, the catalyst was activated by atmospheric pressure for 24 hours at max. 200° C. under hydrogen (25 l (stp)/h) [1 (stp)=liters at standard temperature and pressure=volume converted to standard temperature and pressure conditions (20° C., 1 bar abs.). The starting material mixture of DEOA and ADG was introduced and the reactor was heated to 180° C. The total reaction mixture was then supplied with 200 bar of hydrogen. At various times, samples were taken from the reaction mixture and analyzed by means of gas chromatography. For this, an "RTX-5 amine" GC column 30 m in length was used, with a temperature program: 70° C./5 min, heat to 280° C. at a rate of 5° C./min, at 280° C./10 minutes.

The results of the experiments can be found in Table III below.

TABLE III

| Cat. | Pressure bar | Temp. | Time (h) | DEOA (g) | MR ADG:DEOA mol/mol | Conversion of DEOA | Conversion of ADG | Sel. of HEOEtPIP based on DEOA (mol %) | Sel. of HEOEtPIP based on ADG (mol %) |
|---|---|---|---|---|---|---|---|---|---|
| A | 200 | 180 | 5 | 77 | 1 | 29 | 36 | 6 | 7 |
| A | 200 | 180 | 10 | 77 | 1 | 56 | 62 | 13 | 18 |
| A | 200 | 180 | 15 | 77 | 1 | 81 | 86 | 24 | 36 |

Cat.: Catalyst
MR: Molar ratio in the feed
Sel.: Selectivity (mol %)
Conversion: mol %
HEOEtPIP: 2-(2-Hydroxyethoxy)ethylpiperazine 4. Work-Up The work-up can preferably take place by means of the following five steps (here using the example of a reaction of DEOA with monomethylamine or monoethylamine):
1) Separating off unreacted primary amine (monomethylamine or monoethylamine) and returning it to the reactor
   Optionally removal of some of the monomethylamine or monoethylamine from the top of the column.
2) Separating off water
3) Separating off low-boiling secondary components
4) Pure distillation of the N-alkylpiperazine I overhead while separating off high-boiling secondary components via the bottom.
5) Optionally returning some of the high-boiling secondary components, in particular diethanolamine, N—(N'-methyl-2-aminoethyl)ethanolamine, N-methyl-N-(2-amino-ethyl)ethanolamine (or N—(N'-ethyl-2-aminoethyl)ethanolamine, N-ethyl-N-(2-amino-ethyl)ethanolamine) to the reaction.

The invention claimed is:

1. A process for the preparation of a mono-N-alkylpiperazine of the formula I

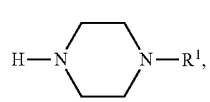

(I)

in which $R^1$ is $C_1$- to $C_5$-alkyl or 2-(2-hydroxyethoxy) ethyl, comprising
reacting diethanolamine of the formula II (DEOA)

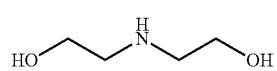

(II)

with a primary amine of the formula $H_2N$—$R^1$ (III) in the presence of hydrogen and a supported, metal-containing catalyst,
wherein a catalytically active mass of the catalyst, prior to its reduction with hydrogen, comprises oxygen-containing compounds of aluminum, copper, nickel and cobalt and, in the range from 0.2 to 5.0% by weight, one or more oxygen-containing compounds of tin, calculated as SnO, and
wherein the reaction is carried out in the liquid phase at an absolute pressure in the range from 95 to 145 bar.

2. The process according to claim 1, wherein the catalytically active mass of the catalyst, prior to its reduction with hydrogen, comprises in the range from 0.4 to 4.0% by weight of oxygen-containing compounds of tin, calculated as SnO.

3. The process according to claim 1, wherein the catalytically active mass of the catalyst, prior to its reduction with hydrogen, comprises in the range from 0.6 to 3.0% by weight of oxygen-containing compounds of tin, calculated as SnO.

4. The process according to claim 1, wherein the catalytically active mass of the catalyst, prior to its reduction with hydrogen, comprises in the range from 5.0 to 35% by weight of oxygen-containing compounds of cobalt, calculated as CoO.

5. The process according to claim 1, wherein the catalytically active mass of the catalyst, prior to its reduction with hydrogen, comprises in the range from 10 to 30% by weight of oxygen-containing compounds of cobalt, calculated as CoO.

6. The process according to claim 1, wherein the catalytically active mass of the catalyst, prior to its reduction with hydrogen, comprises in the range from
   15 to 80% by weight of oxygen-containing compounds of aluminum, calculated as $Al_2O_3$,
   1.0 to 20% by weight of oxygen-containing compounds of copper, calculated as CuO, and
   5.0 to 35% by weight of oxygen-containing compounds of nickel, calculated as NiO.

7. The process according to claim 1, wherein the catalytically active mass of the catalyst, prior to its reduction with hydrogen, comprises in the range from
   30 to 70% by weight of oxygen-containing compounds of aluminum, calculated as $Al_2O_3$,
   2.0 to 18% by weight of oxygen-containing compounds of copper, calculated as CuO, and
   10 to 30% by weight of oxygen-containing compounds of nickel, calculated as NiO.

8. The process according to claim 1, wherein the molar ratio of nickel to copper is greater than 1.

9. The process according to claim 1, wherein no rhenium and/or ruthenium is present in the catalytically active mass of the catalyst.

10. The process according to claim 1, wherein no iron or zinc is present in the catalytically active mass of the catalyst.

11. The process according to claim 1, wherein no oxygen-containing compounds of silicon or of zirconium or of titanium are present in the catalytically active mass of the catalyst.

12. The process according to claim 1, wherein the BET surface area of the catalyst, as determined in accordance with ISO 9277:1995, is in the range from 30 to 250 m²/g.

13. The process according to claim 1, wherein the reaction is carried out at a temperature in the range from 180 to 220° C.

14. The process according to claim 1, wherein the reaction is carried out at an absolute pressure in the range from 100 to 140 bar.

15. The process according to claim 1, wherein the primary amine III is used in a 5- to 15-fold molar amount, based on the DEOA used.

16. The process according to claim 1, wherein aminodiglycol (ADG) is used in a 0.2- to 2-fold molar amount, based on the DEOA used.

17. The process according to claim 1, wherein the catalyst is arranged as a fixed bed in the reactor.

18. The process according to claim 1, wherein the process is carried out continuously.

19. The process according to claim 17, wherein the reaction is carried out firstly at a temperature in the range from 80 to 160° C. and then at a temperature in the range from 180 to 220° C.

20. The process according to claim 17, wherein the reaction takes place in a tubular reactor.

21. The process according to claim 17, wherein the reaction takes place in a circulating-gas mode.

22. The process according to claim 1, wherein the DEOA is used as aqueous solution.

23. The process according to claim 1, wherein the primary amine III is used as aqueous solution.

24. The process according to claim 1, wherein the reaction is carried out at a catalyst hourly space velocity in the range from 0.3 to 0.7 kg of DEOA/($l_{cat.}$·h).

25. The process according to claim 1, wherein the reaction is carried out at a catalyst hourly space velocity in the range from 100 to 1000 liters (stp) of hydrogen/($l_{cat.}$·h).

26. The process according to claim 1, wherein $R^1$ is methyl, ethyl or 2-(2-hydroxyethoxy)ethyl.

27. The process according to claim 1, further comprising distilling a reaction product of the reaction by the steps comprised of,
 (i) optionally separating off overhead unreacted primary amine III,
 (ii) separating water off overhead,
 (iii) optionally separating present by-products with a lower boiling point than that of the mono-N-alkylpiperazine of the formula I off overhead,
 (iv) separating the mono-N-alkylpiperazine of the formula I off overhead, wherein optionally present by-products with a higher boiling point than that of the mono-N-alkylpiperazine of the formula I and optionally present unreacted DEOA remain in the bottom.

28. The process according to claim 27, further comprising
 (v) separating off overhead and returning to the reaction, by distillation, optionally present unreacted DEOA (II) and/or optionally present alkylaminoethylethanolamine as by-product with the formula IV

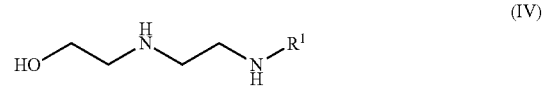

from the bottom of step iv.

29. The process according to claim 27, wherein the unreacted primary amine III separated off in step i is returned to the reaction, and wherein the unreacted primary amine III has a purity of from 90 to 99.9% by weight.

30. The process according to claim 1 for preparing mono-N-alkylpiperazine of the formula I where $R^1$=2-(2-hydroxyethoxy)ethyl, wherein, from the reaction product of the reaction, by distillation, comprising
 (i) first separating water off overhead,
 (ii) optionally separating off overhead unreacted primary amine III (=ADG),
 (iii) optionally separating off overhead present by-products with a lower boiling point than that of the process product I,
 (iv) separating the process product mono-N-alkylpiperazine I off overhead, wherein optionally present by-products having a higher boiling point than that of the process product I and optionally present unreacted DEOA (II) remain in the bottom.

31. The process according to claim 30, further comprising, by distillation,
 (v) separating off overhead any unreacted DEOA and/or any present alkylaminoethylethanolamine as by-product with the formula IV

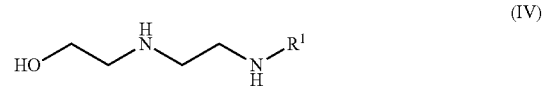

from the bottom of step iv and
 (vi) returning the unreacted DEOA or the alkylaminoethylethanolamine with the formula IV to the reaction.

32. The process according to claim 30, further comprising returning unreacted primary amine III to the reaction, wherein the unreacted primary amine III has a purity of from 90 to 99.9% by weight, and optionally removing some of the unreacted primary amine III.

* * * * *